(12) United States Patent
Groeschke et al.

(10) Patent No.: US 11,862,331 B2
(45) Date of Patent: *Jan. 2, 2024

(54) DEVICE AND METHOD FOR DETECTING AN ACTUATION ACTION PERFORMABLE WITH A MEDICAL DEVICE

(71) Applicant: Sanofi-Aventis Deutschland GMBH, Frankfurt am Main (DE)

(72) Inventors: Jasmin Groeschke, Frankfurt am Main (DE); Hanno Juhnke, Frankfurt am Main (DE); Jan-Peter Spengler, Frankfurt am Main (DE); Matthias Scharf, Frankfurt am Main (DE); Christoph Dette, Frankfurt am Main (DE); Michael Schrack, Pliezhausen (DE); Olaf Zeckai, Weinheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/319,508

(22) Filed: May 13, 2021

(65) Prior Publication Data
US 2021/0265053 A1 Aug. 26, 2021

Related U.S. Application Data

(63) Continuation of application No. 16/572,242, filed on Sep. 16, 2019, now Pat. No. 11,424,026, which is a
(Continued)

(30) Foreign Application Priority Data

Mar. 24, 2011 (EP) ..................................... 11159593

(51) Int. Cl.
*G16H 40/40* (2018.01)
*A61M 5/315* (2006.01)
(Continued)

(52) U.S. Cl.
CPC ........ *G16H 40/40* (2018.01); *A61M 5/31525* (2013.01); *A61M 5/31533* (2013.01);
(Continued)

(58) Field of Classification Search
CPC .............. G16H 40/40; A61M 5/31525; A61M 5/31533; A61M 2005/3142;
(Continued)

(56) References Cited

U.S. PATENT DOCUMENTS 533,575 A 2/1895 Wilkens
4,959,056 A * 9/1990 Dombrowski ...... A61M 5/1782
604/211

(Continued)

FOREIGN PATENT DOCUMENTS

CN 101727540 6/2010
CN 102413855 4/2012
(Continued)

OTHER PUBLICATIONS

[No Author Listed] [online], "Diabetes Education: How to Inject Insulin," available online as of Nov. 14, 2014, URL:<https://www.youtube.com/watch?v=ycp7BbFhG44>, 1 page [Video Submission].

(Continued)

*Primary Examiner* — Nabil H Syed
*Assistant Examiner* — Cal J Eustaquio
(74) *Attorney, Agent, or Firm* — Fish & Richardson P.C.

(57) ABSTRACT

An apparatus is disclosed, comprising a detector unit comprising a detector configured to detect an actuation action performable via the detector unit to an actuation button of a medical device to cause the medical device to eject at least a portion of a medicament comprised in the medical device. The detector is configured to detect the actuation action based on a detection of a force and/or a touch applied to the (Continued)

detector unit as part of the actuation action. The apparatus further comprises an electric unit connected to the detector and configured to store and/or provide information related to the detected actuation action. Furthermore, an according method and a computer program for controlling this method are disclosed.

7 Claims, 2 Drawing Sheets

Related U.S. Application Data continuation of application No. 14/005,877, filed as application No. PCT/EP2012/055252 on Mar. 23, 2012, now Pat. No. 10,446,269.

(51) Int. Cl.
*G16Z 99/00* (2019.01)
*A61M 5/31* (2006.01)

(52) U.S. Cl.
CPC ........... *G16Z 99/00* (2019.02); *A61M 5/3135* (2013.01); *A61M 2005/3126* (2013.01); *A61M 2005/3142* (2013.01); *A61M 2205/52* (2013.01); *A61M 2205/581* (2013.01); *A61M 2205/582* (2013.01); *A61M 2205/583* (2013.01); *A61M 2207/00* (2013.01)

(58) Field of Classification Search
CPC ........ A61M 2205/52; A61M 2205/581; A61M 2205/582; A61M 2205/583; A61M 2207/00
See application file for complete search history.

(56) References Cited

U.S. PATENT DOCUMENTS

| | | |
|---|---|---|
| 5,112,317 A | 5/1992 | Michel |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,331,953 A | 7/1994 | Andersson et al. |
| 5,383,865 A | 1/1995 | Michel |
| 5,480,387 A | 1/1996 | Gabriel et al. |
| 5,505,704 A | 4/1996 | Pawelka et al. |
| 5,509,905 A | 4/1996 | Michel |
| 5,582,598 A | 12/1996 | Chanoch |
| 5,626,566 A | 5/1997 | Petersen et al. |
| 5,662,612 A | 9/1997 | Niehoff |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,246,322 B1 | 6/2001 | LeDain et al. |
| 6,248,095 B1 | 6/2001 | Giambattista et al. |
| 6,277,099 B1 | 8/2001 | Strowe et al. |
| 6,482,185 B1 | 11/2002 | Hartmann |
| 6,500,169 B1 | 12/2002 | Deng |
| 6,585,698 B1 | 7/2003 | Packman et al. |
| 6,620,133 B1 | 9/2003 | Steck |
| 6,869,413 B2 | 3/2005 | Langley et al. |
| 6,899,698 B2 | 5/2005 | Sams |
| 6,936,032 B1 | 8/2005 | Bush, Jr. et al. |
| 7,008,399 B2 | 3/2006 | Larsen et al. |
| 7,241,278 B2 | 7/2007 | Moller |
| 7,749,186 B2 | 7/2010 | Kohlbrenner et al. |
| 8,052,655 B2 | 11/2011 | Moller et al. |
| 8,197,449 B2 | 6/2012 | Nielsen et al. |
| 8,231,573 B2 | 7/2012 | Edwards et al. |
| 8,556,847 B2 | 10/2013 | Kohlbrenner et al. |
| 8,556,865 B2 | 10/2013 | Krulevitch et al. |
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,613,719 B2 | 12/2013 | Karratt et al. |
| 8,672,899 B2 | 3/2014 | Diller et al. |
| 8,771,238 B2 | 7/2014 | Nielsen et al. |
| 8,994,382 B2 | 3/2015 | Nielsen et al. |
| 9,289,559 B2 | 3/2016 | Pedersen et al. |
| 9,522,238 B2 | 12/2016 | Nielsen et al. |
| 9,526,842 B2 | 12/2016 | Oh et al. |
| 9,623,188 B2 | 4/2017 | Nielsen et al. |
| 9,649,448 B2 | 5/2017 | Madsen |
| 9,672,328 B2 | 6/2017 | Saint et al. |
| 9,734,302 B2 | 8/2017 | Nielsen et al. |
| 9,959,391 B2 | 5/2018 | Saint et al. |
| 10,105,489 B2 | 10/2018 | Edwards et al. |
| 10,213,554 B2 | 2/2019 | Andersen et al. |
| 10,383,996 B2 | 8/2019 | Miller et al. |
| 10,420,895 B2 | 9/2019 | Erbstein et al. |
| 10,471,213 B2 | 11/2019 | Schabbach et al. |
| 10,483,000 B2 | 11/2019 | Saint et al. |
| 10,593,232 B2 | 3/2020 | Bauss |
| 10,617,827 B2 | 4/2020 | Hautaviita et al. |
| 10,695,504 B2 | 6/2020 | Nielsen et al. |
| 10,857,304 B2 | 12/2020 | Byerly |
| 10,874,802 B2 | 12/2020 | Toporek et al. |
| 11,020,533 B2 | 6/2021 | Erbstein et al. |
| 11,278,677 B2 | 3/2022 | Erbstein et al. |
| 11,439,762 B2 | 9/2022 | Toporek et al. |
| 11,511,047 B2 | 11/2022 | Toporek et al. |
| 2002/0052578 A1 | 5/2002 | Moller |
| 2002/0120235 A1 | 8/2002 | Enggaard |
| 2002/0123716 A1 | 9/2002 | VanDiver et al. |
| 2002/0143288 A1 | 10/2002 | Larsen et al. |
| 2002/0163435 A1 | 11/2002 | Kosaka |
| 2002/0188419 A1 | 12/2002 | Slate et al. |
| 2003/0036762 A1 | 2/2003 | Kerr et al. |
| 2003/0050609 A1 | 3/2003 | Sams |
| 2003/0208113 A1* | 11/2003 | Mault ............... G16H 40/63 600/316 |
| 2004/0059299 A1 | 3/2004 | Moller |
| 2004/0085215 A1 | 5/2004 | Moberg et al. |
| 2004/0140972 A1 | 7/2004 | Hirota et al. |
| 2004/0210199 A1 | 10/2004 | Atterbury et al. |
| 2004/0254539 A1 | 12/2004 | Wolbring et al. |
| 2004/0267207 A1 | 12/2004 | Veasey et al. |
| 2005/0080384 A1 | 4/2005 | Green |
| 2005/0113765 A1 | 5/2005 | Veasey et al. |
| 2005/0151652 A1* | 7/2005 | Frasch ............... A61M 5/24 235/375 |
| 2005/0182323 A1 | 8/2005 | Grispo et al. |
| 2005/0192530 A1 | 9/2005 | Castellano |
| 2005/0283065 A1 | 12/2005 | Babayoff |
| 2006/0135907 A1 | 6/2006 | Remde et al. |
| 2006/0153693 A1 | 7/2006 | Fiechter et al. |
| 2007/0123829 A1 | 5/2007 | Atterbury et al. |
| 2007/0210828 A1 | 9/2007 | Won et al. |
| 2007/0265579 A1 | 11/2007 | Kleyman et al. |
| 2008/0033369 A1 | 2/2008 | Kohlbrenner et al. |
| 2008/0262469 A1 | 10/2008 | Brister et al. |
| 2009/0043253 A1 | 2/2009 | Podaima |
| 2009/0069742 A1 | 3/2009 | Larsen |
| 2009/0194104 A1 | 8/2009 | Van Sickle |
| 2009/0275916 A1 | 11/2009 | Harms et al. |
| 2010/0114026 A1 | 5/2010 | Karratt et al. |
| 2010/0324496 A1 | 12/2010 | Plumptre et al. |
| 2011/0112474 A1 | 5/2011 | Bochenko et al. |
| 2011/0238017 A1 | 9/2011 | Watanabe et al. |
| 2011/0270214 A1 | 11/2011 | Jorgensen et al. |
| 2011/0313349 A1 | 12/2011 | Krulevitch et al. |
| 2012/0092670 A1 | 4/2012 | Chatow et al. |
| 2013/0197445 A1 | 8/2013 | Schabbach et al. |
| 2013/0204227 A1 | 8/2013 | Bochenko et al. |
| 2013/0274680 A1 | 10/2013 | Veasey et al. |
| 2013/0310756 A1 | 11/2013 | Whalley et al. |
| 2014/0005950 A1 | 1/2014 | Groeschke et al. |

(56) References Cited

U.S. PATENT DOCUMENTS

| | | | |
|---|---|---|---|
| 2014/0194826 A1 | 7/2014 | Nielsen et al. |
| 2014/0194829 A1 | 7/2014 | Baek et al. |
| 2015/0202375 A1 | 7/2015 | Schabbach et al. |
| 2016/0235925 A1 | 8/2016 | Kuhn et al. |
| 2017/0182258 A1 | 6/2017 | Michael |
| 2017/0189625 A1 | 7/2017 | Cirillo et al. |
| 2017/0368263 A1 | 12/2017 | Ploch |
| 2018/0001027 A1 | 1/2018 | Klemm et al. |
| 2018/0008778 A1 | 1/2018 | Erbstein et al. |
| 2018/0154086 A1 | 6/2018 | Toporek et al. |
| 2019/0381248 A1 | 12/2019 | Erbstein et al. |
| 2020/0147315 A1 | 5/2020 | Toporek et al. |
| 2020/0197614 A1 | 6/2020 | Erbstein et al. |
| 2020/0353176 A1 | 11/2020 | Toporek et al. |
| 2020/0384205 A1 | 12/2020 | Toporek et al. |
| 2022/0001111 A1 | 1/2022 | Toporek et al. |
| 2022/0134009 A1 | 5/2022 | Erbstein et al. |

FOREIGN PATENT DOCUMENTS

| | | |
|---|---|---|
| CN | 102458514 | 5/2012 |
| CN | 103561801 | 2/2014 |
| CN | 104203315 | 12/2014 |
| CN | 104245020 | 12/2014 |
| CN | 104411349 | 3/2015 |
| CN | 103648555 | 3/2019 |
| DE | 29904864 | 8/2000 |
| DE | 102004063664 | 7/2006 |
| EP | 0777123 | 6/1997 |
| EP | 0937471 | 8/1999 |
| EP | 0937476 | 8/1999 |
| EP | 2060284 | 5/2009 |
| EP | 2182456 | 5/2010 |
| EP | 2692378 | 2/2014 |
| EP | 2762184 | 8/2014 |
| EP | 3304372 | 12/2018 |
| EP | 2401012 | 4/2020 |
| JP | H11-267207 | 10/1999 |
| JP | 2000-506030 | 5/2000 |
| JP | 2001-087386 | 4/2001 |
| JP | 2001-509426 | 7/2001 |
| JP | 2004-523282 | 8/2004 |
| JP | 2008-516711 | 5/2008 |
| JP | 2009-530002 | 8/2009 |
| JP | 2010-534085 | 11/2010 |
| JP | 2012-500695 | 1/2012 |
| JP | 2012-504440 | 2/2012 |
| JP | 2012-135594 | 7/2012 |
| JP | 2012-519025 | 8/2012 |
| JP | 2012-519028 | 8/2012 |
| JP | 2014-516599 | 7/2014 |
| JP | 2014-520584 | 8/2014 |
| JP | 2014-533537 | 12/2014 |
| WO | WO 1990/009202 | 8/1990 |
| WO | WO 1993/016743 | 9/1993 |
| WO | WO 1997/030742 | 8/1997 |
| WO | WO 1999/002210 | 1/1999 |
| WO | WO 1999/038554 | 8/1999 |
| WO | WO 2001/010484 | 2/2001 |
| WO | WO 2002/058767 | 8/2002 |
| WO | WO 2002/064196 | 8/2002 |
| WO | WO 2006/045525 | 5/2006 |
| WO | WO 2007/107564 | 9/2007 |
| WO | WO 2009/013736 | 1/2009 |
| WO | WO 2009/083600 | 7/2009 |
| WO | WO 2010/023303 | 3/2010 |
| WO | WO 2010/037828 | 4/2010 |
| WO | WO 2010/052275 | 5/2010 |
| WO | WO 2010/098927 | 9/2010 |
| WO | WO 2010/098928 | 9/2010 |
| WO | WO 2010/098931 | 9/2010 |
| WO | WO 2010/128493 | 11/2010 |
| WO | WO 2010/142598 | 12/2010 |
| WO | WO 2012/046199 | 4/2012 |
| WO | WO 2012/118687 | 9/2012 |
| WO | WO 2012/127046 | 9/2012 |
| WO | WO 2012/130703 | 10/2012 |
| WO | WO 2013/004844 | 1/2013 |
| WO | WO 2013/072445 | 5/2013 |
| WO | WO 2013/120774 | 8/2013 |
| WO | WO 2013/120777 | 8/2013 |
| WO | WO 2013/120778 | 8/2013 |
| WO | WO 2013/177135 | 11/2013 |
| WO | WO 2014/023763 | 2/2014 |
| WO | WO 2014/037331 | 3/2014 |
| WO | WO 2014/064691 | 5/2014 |
| WO | WO 2014/111337 | 7/2014 |
| WO | WO 2014/128156 | 8/2014 |
| WO | WO 2014/173768 | 10/2014 |
| WO | WO 2014/173774 | 10/2014 |
| WO | WO 2014/180744 | 11/2014 |
| WO | WO 2014/180745 | 11/2014 |
| WO | WO 2016/131713 | 8/2016 |
| WO | WO 2016/193229 | 12/2016 |
| WO | WO 2019/173097 | 9/2019 |

OTHER PUBLICATIONS

[No Author Listed] [online], "How to use SoloStar Pen for Injecting Lantus (Glargine) and Apidra (Glulisine) Insulin Music Version," available online as of May 17, 2013, URL:<https://www.youtube.com/watch?v=ZcfKG0Mp3kI>, 1 page [Video Submission].
[No Author Listed], "Comparison of publication EP201012B1 with publication WO2010/098928," cited in European Opposition in EP Application No. 16729241.6, unknown date, 26 pages.
Brief Communication in European Application No. 16729241.6, dated Apr. 11, 2022, 28 pages.
Brief Communication in European Application No. 16729241.6, dated Apr. 7, 2022, 11 pages.
Brief Communication in European Application No. 16729241.6, dated Apr. 7, 2022, 22 pages.
Written Submission in European Opposition in European Application No. 16729241.6, dated Apr. 4, 2022, 30 pages.
EP Notice of Opposition by Di-Care Zrt. in Patent Application No. 16729241.6, dated Feb. 8, 2021, 17 pages.
Brief Communication in European Application No. 12710104.6, dated May 6, 2022, 37 pages.
Brief Communication in European Application No. 16704003.9, dated May 5, 2022, 152 pages.
dictionary.cambridge.org [online], "Button," 2014, retrieved on Jan. 3, 2022, retrieved from URL <https://dictionary.cambridge.org/de/worterbuch/englisch/button>, 11 pages.
EP Notice of Opposition by Ferring International Center S.A. in Patent Application No. 9737825.1, dated Jun. 18, 2013, 22 pages.
EP Response to Communication in Opposition by Herzog IP Patentanwalts GMBH in Patent Application No. 16704003.9, dated Jun. 19, 2019, 7 pages.
[No Author Listed] [online], "'NovoPen 5—Novo Nordisk,'" Youtube, Jul. 5, 2012, retrieved on Sep. 10, 2021, <https://www.youtube.com/watch?v=u3EX_0KzkQE>, 1 page [Video Submission].
[No Author Listed], "HumaPen Ergo Manual", Eli Lilly and Company Ltd., 2003, 2 pages.
[No Author Listed], "Technical Dossier for the HumaPen Pen-Injector Family," Eli Lilly & Company—Pharmaceutical Delivery Systems, Aug. 15, 2000, 17 pages.
EP Notice of Opposition by Di-Care Zrt. in Patent Application No. 16704003.9, dated Aug. 27, 2021, 33 pages.
EP Notice of Opposition by Herzog IP Patentanwalts GmbH in Patent Application No. 12710104.6, dated Aug. 31, 2021, 50 pages.
EP Notice of Opposition by Herzog IP Patentanwalts GMbH in Patent Application No. 16704003.9, dated Aug. 31, 2021, 126 pages.
*Novo Nordisk A/S*, Plaintiff, v. *Sanofi-Aventis U.S. LLC and Sanofi-Aventis*, Defendants, Case No. 3:07-cv-03206-MLC-JJH, Affidavit of Charles E. Clemens, filed Sep. 10, 2007, 82 pages.
Rustige, "Important New Safety Reminder Regarding the HumaPen Ergo", HumaPen Ergo Customer letter from Eli Lilly Canada, Dec. 11, 2001, 2 pages.

(56) References Cited

OTHER PUBLICATIONS

Brief Communication in European Application No. 12710104.6, dated Jan. 20, 2022, 70 pages.
Brief Communication in European Application No. 16704003.9, dated Jan. 21, 2022, 81 pages.
[No. Author Listed] [online], "Injecting Insulin With the Lantus SoloSTAR Pen," available online as of Oct. 29, 2012, URL :< https://www.youtube.com/watch?v=g7JLG36ZO-U>, 2012, 1 page [Video Submission].
EP Extended Search Report in European Patent Application No. 15171252.8, dated Dec. 9, 2015, 7 pages.
EP Search Report in European Patent Application No. 15155758.4, dated Sep. 4, 2015, 3 pages.
European Search Report for EP Application No. 12710104.6, dated Sep. 21, 2017.
PCT International Preliminary Report on Patentability in Application No. PCT/EP2012/055252, dated Sep. 24, 2013, 9 pages.
PCT International Preliminary Report on Patentability in International Appln. No. PCT/EP2016/052987, dated Aug. 22, 2017, 7 pages.
PCT International Preliminary Report on Patentability in International Appln. No. PCT/EP2016/063139, dated Dec. 12, 2017, 7 pages.
PCT International Search Report and Written Opinion in International Appln. No. PCT/EP2016/052987, dated Apr. 21, 2016, 10 pages.
PCT International Search Report and Written Opinion in International Appln. No. PCT/EP2016/063139, dated Sep. 22, 2016, 12 pages.
PCT International Search Report for International Application No. PCT/EP2012/055252, completed Oct. 31, 2012.
U.S. Appl. No. 15/551,971, filed Aug. 18, 2017, Frank Erbstein.
U.S. Appl. No. 16/555,772, filed Aug. 29, 2019, Frank Erbstein.
U.S. Appl. No. 16/806,810, filed Mar. 2, 2020 Frank Erbstein.
U.S. Appl. No. 15/579,656, filed Dec. 5, 2017, Maurice Toporek.
U.S. Appl. No. 16/742,219, filed Jan. 14, 2020, Maurice Toporek.
U.S. Appl. No. 16/938,433, filed Jul. 24, 2020, Maurice Toporek.
U.S. Appl. No. 17/001,065, filed Aug. 24, 2020, Maurice Toporek.
U.S. Appl. No. 14/005,877, filed Sep. 18, 2013, Jasmin Groeschke.
U.S. Appl. No. 16/572,242, filed Sep. 16, 2019, Jasmin Groeschke.
Brief Communication in European Application No. 12710104.6, dated Jan. 9, 2023, 47 pages.
Novo Nordisk, "How to use NovoPen® 4," [No Publication Date Listed], 2 pages (English version).
Novo Nordisk, "Instruction Manual for the NovoPen® 4," 2004, 17 pages (Polish version).
Novo Nordisk, "Instruction Manual for the NovoPen® 4," 2004, 19 pages (German version).
Pearson et al., "Practical Aspects of Insulin Pen Devices," Journal of Diabetes Science and Technology, May 2010, 4(3):522-531.
Interlocutory decision in Opposition Proceedings in European Application No. 16729241.6, dated Sep. 22, 2022, 231 pages.
EP Reply to a Submission in Opposition by Herzog IP Patentanwalts GMbH in Patent Application No. 12710104.6, dated Jan. 27, 2023, 162 pages.
Brief Communication in European Appln. No. 12710104.6, dated Mar. 13, 2023, 13 pages.
Decision Rejecting the Opposition in European Application No. 12710104.6, dated May 11, 2023, 62 pages.
Examination Report in European Appln. No. 12710104.6, dated Sep. 21, 2017, 6 pages.
Ondrugdelivery, "Delivering Injectables: Devices & Device Components," ONdrugDelivery Ltd., 2007, 20 pages.
Reply to Examination Report in European Appln. No. 12710104.6, dated Jun. 29, 2018, 6 pages.

\* cited by examiner

DEVICE AND METHOD FOR DETECTING AN ACTUATION ACTION PERFORMABLE WITH A MEDICAL DEVICE

CROSS REFERENCE TO RELATED APPLICATIONS

The present application is a continuation of U.S. patent application Ser. No. 16/572,242, filed Sep. 16, 2019, which is a continuation of U.S. patent application Ser. No. 14/005,877, filed Sep. 18, 2013, now U.S. Pat. No. 10,446,269, which is a U.S. National Phase Application pursuant to 35 U.S.C. § 371 of International Application No. PCT/EP2012/055252, filed Mar. 23, 2012, which claims priority to European Patent Application No. 11159593.0 filed Mar. 24, 2011. The entire disclosure contents of these applications are herewith incorporated by reference into the present application.

TECHNICAL FIELD

The present invention relates to an apparatus and a method for detecting an actuation action that is performable with a medical device to cause the medical device to eject a medicament that is comprised in the medical device. The invention further relates to a computer program for controlling such a method.

BACKGROUND

A variety of diseases exists that require regular treatment by injection or infusion of a medicament with a medical device that ejects this medicament. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an actuation button of the insulin pen.

It is desirable to provide such medical devices for ejection of medicaments with functionality beyond their basic medicament ejection capabilities, such as for instance functionality to monitor use and/or to prevent false handling (for instance untimely reuse) of the medical devices. This requires detection of actuation actions performed with the medical device.

International patent application publication WO 2007/107564 A1 discloses a method and an electronic module for monitoring the operation of a medication delivery device. An electronic module is releasably arranged in the vicinity of the medication delivery device and used to detect measurable acoustical or vibrational signals generated in response to an action occurring within the medication delivery device. Information associated with or representing the measured signals is then stored.

However, such measurement of acoustical signals (such as for instance sounds generated when dialing or ejecting a dose) may not be reliable enough in noisy environments. The same holds for the detection of vibrational signals in mobile environments.

SUMMARY

It is thus inter alia an object of the present invention to provide an apparatus and a method for reliable detection of actuation actions performed with a medical device. Similarly, a computer program controlling such a method is sought.

According to a first aspect of the present invention, an apparatus is disclosed. The apparatus comprises a detector unit comprising a detector configured to detect an actuation action performable via the detector unit to an actuation button of a medical device to cause the medical device to eject at least a portion of a medicament comprised in the medical device. Therein, the detector is configured to detect the actuation action based on a detection of a force and/or a touch applied to the detector unit as part of the actuation action. The apparatus further comprises an electric unit connected to the detector and configured to store and/or provide information related to the detected actuation action.

According to a second aspect of the present invention, a method is disclosed. The method comprises detecting, with a detector, an actuation action performable via a detector unit that comprises the detector to an actuation button of a medical device to cause the medical device to eject at least a portion of a medicament comprised in the medical device, wherein the detector is configured to detect the actuation action based on a detection of a force and/or a touch applied to the detector unit as part of the actuation action. The method further comprises storing and/or providing information related to the detected actuation action.

Also an apparatus configured to perform the method according to the second aspect of the present invention shall be considered to be disclosed.

According to a third aspect of the present invention, furthermore a computer program is disclosed, comprising instructions operable to cause a processor to control the steps of the method according to the second aspect of the present invention when the computer program is executed on the processor. The computer program may for instance be storable or encodable in a computer-readable medium. The computer program may for instance at least partially represent software and/or firmware of the processor. The processor may for instance be or be part of the electric unit of the apparatus.

According to a fourth aspect of the present invention, furthermore a computer-readable medium is disclosed, having a computer program according to the third aspect of the present invention stored thereon. The computer-readable medium may for instance be embodied as an electric, magnetic, electro-magnetic, optic or other storage medium, and may either be a removable medium or a medium that is fixedly installed in an apparatus or device. Non-limiting examples of such a computer-readable medium are a Random-Access Memory (RAM) or a Read-Only Memory (ROM). The computer-readable medium may for instance be a tangible medium, for instance a tangible storage medium. A computer-readable medium is understood to be readable by a computer, such as for instance a processor.

In the following, features and embodiments (exhibiting further features) of the present invention will be described, which are understood to equally apply to all aspects of the present invention. These single features/embodiments are considered to be exemplary and non-limiting, and to be respectively combinable independently from other disclosed features/embodiments with the apparatus, method, computer program and computer-readable medium of the present invention as described above. Nevertheless, these features/ embodiments shall also be considered to be disclosed in all possible combinations with each other and with the apparatus, method, computer program and computer-readable medium of the present invention as described above.

The medical device is configured to eject a medicament (non-limiting examples of a medicament, also frequently referred to as a "drug", are a substance that, when absorbed into the body of a living organism, alters normal bodily function; a substance used in the treatment, cure, prevention, or diagnosis of disease or used to otherwise enhance physical or mental well-being of a creature; or a pharmaceutical formulation containing at least one pharmaceutically active compound). The ejected drug or medicament may for instance be in a solid (e.g. a powder), liquid or gaseous state, or may comprise a mixture of components in solid, liquid and/or gaseous states, such as an aerosol.

The ejected medicament may for instance be at least partially (for instance completely) administered (for instance by way of injection or infusion) into material, e.g. a body of a creature (for instance a human being or an animal). Non-limiting examples of the medical device are thus an injection device (such as an injection pen) or an infusion device (such as an infusion pump). Therein, an injection process may for instance be differentiated from an infusion process inter alia based on the time each process takes (For instance, an injection process may have a significantly smaller duration (e.g. less than 5 minutes) as compared to an infusion process). The administering of the medicament may for instance be executed with the medical device by an entity (a human being or a machine). The human being executing the administering of the medicament may then for instance be a patient receiving the medicament, or another person, such as a member of health personnel, such as doctor or a nurse. An example of a medicament to be administered with the medical device is insulin.

The medical device may for instance be a disposable device that is designed for a limited number of ejection processes and subsequent disposal. The medical device may for instance be pre-filled and non-refillable, so that it has to be disposed after all of or substantially all of the medicament (s) contained therein has been injected (as a one-way device). Equally well, the medical device may be equipped with exchangeable containers comprising the medicament to be injected. The medical device may for instance be a pen-shaped injection device with an injection needle at one end and an actuation button at the other end. The actuation button may for instance protrude from the medical device (for instance at one end thereof) so that it can be actuated by a user by pressing it.

The actuation action causing the medical device to eject at least a portion of the medicament may for instance be applying an actuation force to the actuation button.

The medical device may for instance be a mechanical device (e.g. a purely mechanical device), which is caused to eject at least a portion of the medicament comprised therein if an actuation force is applied to the actuation button of the medical device. The actuation force may for instance be lead to a piston of a medicament container (which may comprise the medicament directly may comprise a cartridge that contains the medicament) and may cause a portion of the medicament to be ejected through a needle of the medical device.

Alternatively, the medical device may for instance be an at least partially electric medical device, wherein applying an actuation force (which may for instance be smaller than an actuation force applied to a mechanical medical device) to the actuation button triggers ejection of at least a portion of the medicament, for instance by an electric pump.

The actuation action is for instance performed by a human or non-human user of the medical device, for instance by a patient that is to receive the medicament comprised in the medical device, or by medical personnel. The actuation action may for instance by applied by a finger or thumb of a human user.

According to embodiments of the present invention, the actuation action is detected by a detector that is comprised in a detector unit. To this end, the detector unit is arranged with respect to the actuation button in a way that the actuation action has to be performed to the actuation button at least partially via the detector unit. The detector unit may for instance at least partially be placed on top of the actuation button or may for instance form an upper part of the actuation button itself. Instead of a surface of the actuation button, then for instance at least a part of the surface of the detector unit may become the surface where the actuation force has to be applied.

The detector unit may for instance be the detector itself. Equally well, the detector unit may comprise further elements. For instance, the detector unit may be or comprise a housing that at least partially surrounds the detector. The detector unit may comprise further parts, for instance parts that relay an actuation force applied via the detector unit to the actuation button. Parts of the detector unit may be coupled to the detector to allow the detector to detect the actuation action applied to the actuation button via the detector unit. The detector unit may for instance have to be robust enough to relay an actuation force applied via the detector unit to the actuation button.

The detector is configured to detect the actuation action based on a detection of a force and/or a touch applied to the detector unit as part of the actuation action.

As an example, the detector may be an electric switch with an actuator (e.g. a snap element or a pin) that forms part of or protrudes out of the detector unit (e.g. a housing or base that supports the detector from below) in a way that the actuator is moved downwards or inwards when a force is applied to the actuation button via the detector unit as part of the actuation action (e.g. an actuation force) and thus closes the electric switch. The actuator may for instance be covered by a membrane, which is part of the detector unit, to prevent pollution of the interior of the detector unit from outside. The electric switch may for instance comprise a return element (like for instance a spring) that causes the switch to open again once the force is no longer applied.

As another example, the detector may be a piezoelectric sensor that is comprised in the detector unit (e.g. a housing or a base that supports the detector from below) in a way that at least one of its surfaces directly or indirectly (e.g. via a membrane of the detector unit) receives the force forming part of the actuation action (e.g. an actuation force) and it thus able to detect it.

As a further example, the detector may be a pressure sensor contained in the detector unit (which may for instance be a sealed housing) in a way that a deformation of the detector unit (or movement of parts of the detector unit) in response to the force forming part of the actuation action (e.g. an actuation force) causes pressure differences in the detector unit and thus allows the detector to detect the actuation force.

As a further example, the detector may be a touch sensor, e.g. an electric or thermal or optical touch sensor, to name but a few examples. The touch sensor may for instance be the detector unit or may be arranged at a position of the detector unit in a way that it has to be touched when the actuation action shall be performed. For instance, when the actuation action is applying an actuation force, the touch sensor may be arranged at a position of the detector unit where the actuation force is applied.

Detection of the actuation action may for instance be of binary nature, so that it is only detected if an actuation action is performed or not. Therein, an actuation action may for instance only be considered to be present if a force component thereof exceeds a pre-defined force threshold and/or if a touch component thereof persists longer than a pre-defined time duration.

The electric unit is connected to the detector, for instance by a wired connection, and configured to store and/or provide information related to the detected actuation action. Therein, the information may for instance be provided to a user of the medical device, for instance visually, acoustically, haptically or by means of vibration, and/or may be provided to an electronic device, such as for instance a mobile phone or a computer.

The electric unit may for instance be an electric circuit. In a comparably simple embodiment, the electric circuit implements a timer that is activated when an actuation action is detected and then causes and/or generates an indication on the detected actuation action (e.g. causes an LED to be turn on) for a pre-determined duration of time. After the time, the indication stops (e.g. the LED is turned of). In more complex embodiments, the electric unit may comprise a processor and optionally further functional units, like for instance a wireless transmission module or a display module.

According to embodiments of the present invention, thus instead of an acoustic or vibrational detection of actions performed with the medical device, a detection of actuation actions based on a force and/or a touch applied to the actuation button of the device via the detector unit is performed, which is generally much more robust. Since the force and/or the touch have to be performed by a user of the medical device as part of the actuation action anyway, no additional handling steps are required. Information on the detected actuation action is then for instance provided to a user of the medical device and/or to another entity to inform the user and/or the other entity on the actuation action. In this way, for instance a current status and/or a history of an application procedure performed with the medical device can be indicated. This supports a user and/or the other entity with respect to handling of the medical device and contributes to product safety.

According to an embodiment of the invention, the force acts on the detector directly or via at least a part of the detector unit, or is detected by the detector because the detector is responsive to a movement and/or a deformation of at least a part of the detector unit caused by the force.

The force may for instance act directly on an actuator (e.g. a snap element or pin) of an electric switch that forms part of or protrudes out of the detector unit, or may directly act on a piezoelectric sensor. Equally well, the force may act on an electric switch or a piezoelectric sensor via a membrane of the detector unit. The force may equally well be relayed to the sensor (e.g. an electric or optical switch or a piezoelectric sensor) via parts or components of the detector unit that are movably mounted in the detector unit. The force may also be detected based on a deformation of the detector unit, which may cause a change in the pressure of the (sealed) detector unit that is detectable by a pressure sensor within or coupled to the detector unit.

According to an embodiment of the apparatus according to the first aspect of the invention, the apparatus comprises an attachment unit for fixedly or releasably attaching the apparatus to the medical device.

The apparatus may for instance be considered to be fixedly attached to the medical device if it can only be removed from the medical device under destruction of at least a part of the medical device and/or of at least a part of the apparatus. The apparatus may for instance be considered to be releasably attached to the medical device if it can be removed from the medical device without destruction of the medical device and the apparatus, for instance in a way that the apparatus can subsequently be attached to the medical device or another medical device again. Non-limiting examples of an attachment unit are components that allow for a form closure, fit closure, screw coupling or Velcro-like coupling between the apparatus and the medical device. For instance, the attachment unit may be configured to engage with or at least partially embrace the medical device, for instance with one or more arms, clips or rings.

The apparatus thus may for instance be a module that is attached to the medical device after manufacturing of the medical device is completed (or for instance as the last production step). The apparatus may for instance be attached to the medical device by a user of the medical device. The apparatus may for instance comprise pre-stored information on the medical device to which it can be attached (like for instance the type of medicament contained therein, and/or the amount of medicament contained therein). The apparatus may for instance be designed in such a way that it can only be attached to specific medical devices, and that attachment to other medical devices (for instance with medical devices that contain another medicaments) is not possible. This may for instance be achieved by different designs of the attachment unit and/or of the portions of the medical devices to which the apparatus can be attached to. For instance, apparatuses for different medical devices may be provided with different protrusions in their attachment units that cooperate with grooves on the portions of the medical devices to which the apparatuses shall be attached. Attachment of an apparatus may then only be possible if the protrusion of the apparatus matches the groove on the medical device.

The attachment unit may for instance be adapted to fit on an outer circumference of at least a portion of the medical device, for instance by form closure, fit closure, or screw coupling. The portion of the medical device may for instance be at least a portion of the actuation button, for instance an upper end thereof, or at least a portion of a dosage selector (such as for instance a ring-shaped dosage knob that is rotated around a longitudinal axis of the medical device to select a dose), or at least a portion of a housing of the medical device (for instance a part of the housing below a dose selector of a medical device).

A housing of the detector unit may for instance be coupled to or integrally formed with the attachment unit. For instance, the housing may have a cylindrical or conical form, wherein a lower part of the housing forms the attachment unit, for instance with an opening at the lower end to be placed on top of the actuation button, and an upper part of the housing forms at least a part of the detector unit. The detector may then be arranged within an opening at the upper end of the housing, for instance in a way that it is at least partially covered by the housing or by a membrane attached to the housing.

According to an embodiment of the invention, the detector is one of an electric switch, a piezoelectric sensor, an optical sensor, a pressure sensor and a touch sensor.

According to an embodiment of the invention, the information related to the detected actuation action is information related to an instant of time at which the actuation action is detected. The instant of time may for instance be displayed, for instance via a display element of the apparatus, to indicate to a user when the medical device was used the last time, and thus to prevent to early re-use of the medical device, for instance in case that a user forgot that he already used the medical device.

According to an embodiment of the invention, the information related to the detected actuation action is a representation of a time instant at which the actuation action is detected, or a representation of a time duration that has passed since the actuation action was detected, or an information that a pre-defined time duration since the actuation action was detected has already passed or not.

According to an embodiment of the apparatus according to the first aspect of the invention, the electric unit is configured to determine a length of a time interval during which the actuation action is applied, and to store and/or provide information related to the determined length of the time interval and/or to store and/or provide the information related to the detected actuation action in dependence on the determined length of the time interval. The length of the time interval may for instance be indicative of the type of action that was performed with the medical device. For instance, a time interval with a length above a pre-defined threshold (for instance 2 or 5 seconds) may indicate that the medical device was used for an injection/infusion, whereas a time interval with a length below the pre-defined threshold may indicate that a priming operation was performed with the medical device. In the latter case, for instance no information on the detected actuation action may be stored and/or provided. A priming (or commissioning) of the medical device may for instance be performed when using the medical device for the first time or after a change of a medicament container. In the priming operation, only a comparably small number of units of the medicament is ejected.

According to an embodiment of the apparatus according to the first aspect of the invention, the electric unit further comprises a provision unit configured to provide information on the information related to the detected actuation action optically, acoustically, haptically, by vibration, or by transmission to an electronic device that is different from the medical device. The information may for instance be displayed via a display or via one or more light sources, such as for instance Light Emitting Diodes (LEDs). Therein, for instance different colours may convey different information. As an example, if a time duration since a last detected actuation action is below a pre-defined threshold, a red light may be shown, whereas if the time duration since the last detected actuation action is above the pre-defined threshold, a green light may be shown. The red light then may indicate that the medical device should not be used, whereas the green light indicates that the medical device can be used again. This may for instance prevent too early re-use of the medical device, for instance in cases where a user forgot that he/she already used the medical device shortly before.

Equally well, the information on the information related to the detected actuation action may be transmitted to the electronic device, for instance by wireless (e.g. optical or radio transmission, such as for instance a Bluetooth transmission) or wirebound transmission. In the latter case, the electric unit of the apparatus may for instance comprise an interface for a cable to be connected, such as for instance a Universal Serial Bus (USB) interface. The electronic device may for instance be a mobile phone or a computer, where for instance a log on the actions performed with the medical device may be kept.

Therein, the electronic device may for instance be configured to store the information, for instance in the form of a logbook or archive, and/or to use the information to monitor use of the medical device (for instance to launch an alert if improper handling of the medical device is detected), and/or to use the information (and potentially further information) to determine a proposal of the next type and/or dose of medicament to be administered, optionally with a proposal for the time instant when the dose should be applied. In an example embodiment, such information may be provided back to the apparatus and may optionally be displayed to a user of the apparatus.

The electronic device may for instance be or at least implement (for instance via an application (such as a mobile phone application available on or via the internet) that can be installed to the electronic device to enhance its functionality) a blood glucose monitoring system, which may for instance reveal individual patterns of blood glucose changes and may help in the planning of meals, activities, and at what time of day to take medicaments or to administer a medicament.

The blood glucose monitoring system may for instance comprise a blood glucose meter for measuring the blood glucose level of the patient that uses the medical device, or may (for instance regularly or irregularly) receive information on this blood glucose level from a blood glucose meter. The blood glucose meter may for instance measure the blood glucose level based on a drop of blood placed on a disposable test strip which interfaces with a digital meter.

Provision of the information on the information related to the detected actuation action may be triggered by a user (e.g. by pushing a button of the apparatus) or automatically, for instance in response to a detection of an actuation action, or on a regular or irregular basis that can be defined by a user of the apparatus.

In addition to the information on the information related to the detected actuation action, further information may be provided by the apparatus (or its provision unit). Non-limiting examples of such information is information related to the type and/or original or current amount of medicament contained in the medical device, an expiration date of the medicament contained in the medical device, a time instant of a first actuation action detected (or a time duration since this first detected actuation action) for the medical device (potentially after a resetting operation performed with the electric unit), and a time instant since a resetting operation performed with the electric unit. At least a part of this information may for instance be pre-stored in the apparatus, and/or may be programmed into the apparatus by a user via a wireless or wirebound interface or via a user-interface of the apparatus (which, in the simplest case, may for instance only be a button).

According to an embodiment of the apparatus according to the first aspect of the invention, the apparatus further comprises a dose determination unit configured to determine a dose of the medicament selected before the actuation action is applied, wherein the dose determination unit is connected to the electric unit and wherein the electric unit is further configured to store and/or provide information related to the determined dose and/or to store and/or provide the information related to the detected actuation action in dependence on the determined dose. For instance, if the determined dose is below a pre-determined threshold, the actuation action may be classified as a priming action only, and no information on the detected actuation action and/or the determined dose may be stored and/or provided.

The dose determination unit may for instance be configured to determine the dose by sensing sounds that occur when a dose selector of the medical device is operated (for instance sounds caused by mechanical elements of the medical device moving with respect to each other during dose selection), or by sensing a movement of the dose selector. The movement may comprise a rotational movement, a linear movement, or a combination of a rotational and a linear movement, for example a helical movement, and/or the like. In case of an injection pen, the movement may be a rotational or a helical movement. The rotational component of the movement may for instance be determined optically based on a ratchet disk that is affixed to the dose selector and a cooperating light barrier, or by a toothed disk affixed to the dose selector and a cooperating electric switch.

According to an embodiment of the apparatus according to the first aspect of the invention, the electric unit is further configured to provide information allowing for identifying, locating or finding the medical device. The information may for instance be provided in response to a reception of a triggering signal (for instance a radio signal or an acoustic signal like a whistle), or under the control of the electric unit, for instance periodically.

These and further concepts of the invention will be apparent from and elucidated with reference to the detailed description presented hereinafter.

DETAILED DESCRIPTION

Figure 1:
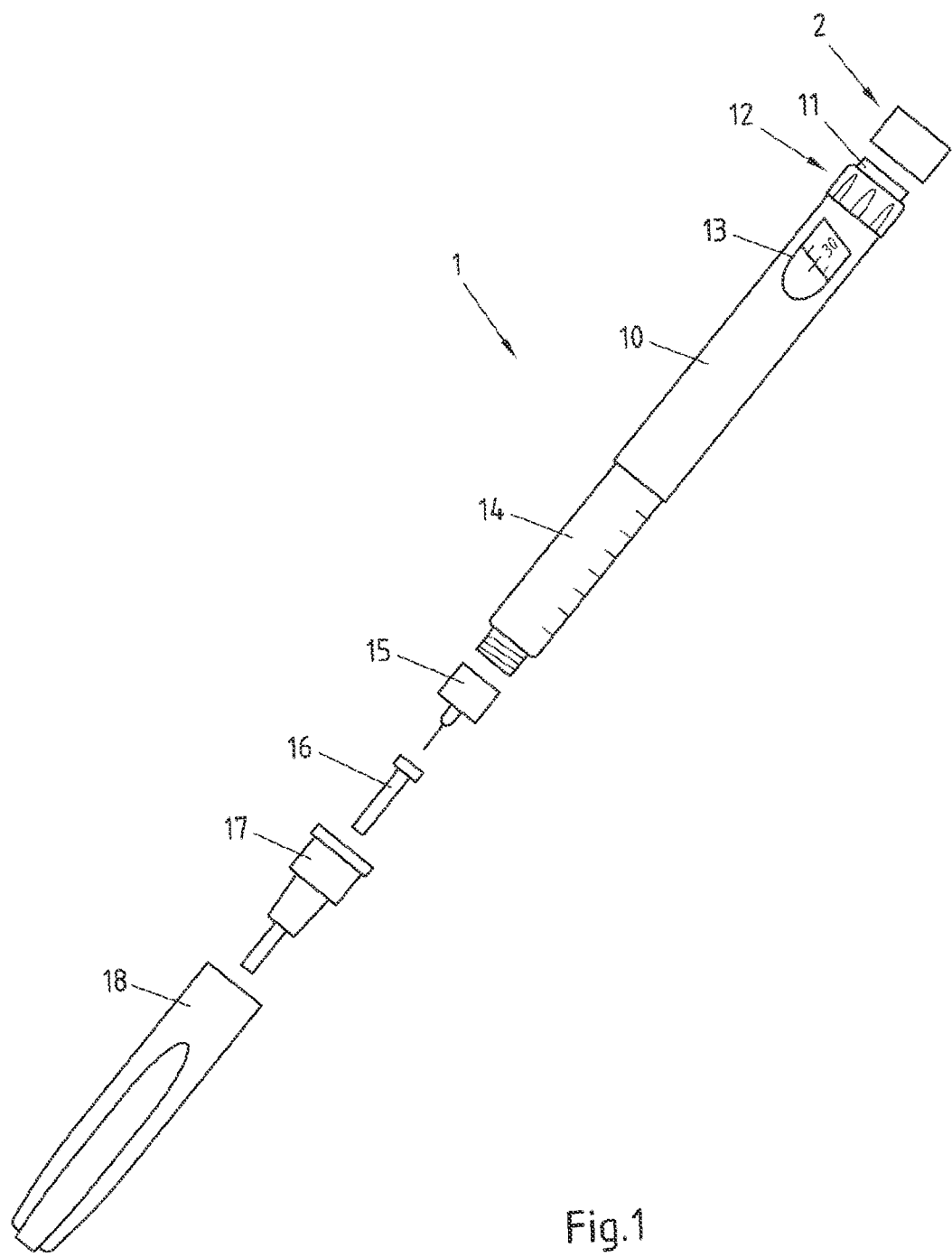
FIG. 1 is an exploded view of an injection device and an embodiment of an apparatus according to the present invention.

Embodiments of the present invention inter alia address the need for enhancement of purely mechanical one-way or multi-way/re-usable injection/infusion products, such as insulin injection pens), which do not provide a power supply, with additional functions, such as for instance a usability indication, an alarm function or patient-specific therapy functions.

Since native integration of such additional functions into injection/infusion products increases their costs, it is generally desirable to provide such functions based on an additional add-on module.

Due to the complexity and criticality of infusion/injection devices, it is advantageous that such an add-on module is provided without requiring constructional changes of the infusion/injection devices to which it shall be added.

Furthermore, it is advantageous (e.g. cost-efficient) that the add-on module can be easily and quickly attached to the infusion/injection devices with only minor change of production lines for the infusion/injection devices (in case that the add-on module is attached to the infusion/injection devices as the last or one of the last production steps) or by hand assembly (for instance by a user of the infusion/injection device itself), even in case of low quantities.

Embodiments of the present invention allow for easy and cost-efficient addition of functions (for instance supported by a power source such as for instance a battery) to medical devices. These functions may for instance comprise one or more of:

- indicating the time since the last application or until the next application (for instance optically or acoustically),
- reminding of a time (for instance optically, acoustically or by means of vibration),
- indicating usability (for instance optically, acoustically or by means of vibration), and/or
- allowing identification (for instance via Radio Frequency Identification, RFID).

Modules/apparatuses according to embodiments of the present invention may for instance be attached to the medical devices in one or more of the following forms:

- The attachment may be persistent (fixedly, i.e. non-releasably), for instance as an additional production step during manufacturing of the medical device and/or the module. For instance, the module may be clicked on a dosage knob or actuation button of a medical device, or may be attached to the medical device via a snap/latch mechanism, allowing for cost-efficient automatic assembly or assembly by hand.
- The attachment may be persistent (fixedly) for each medical device, but may be accomplished by the user of the medical device.
- The attachment is releasably (e.g. only temporary). The module may then for instance be transferrable from medical device to medical device and thus be reusable, yielding cost savings for the user.

Modules/apparatuses according to embodiments of the present invention may for instance comprise one or more of the following components:

- a power unit,
- a housing with a (standardized) attachment unit for attachment to a medical device,
- a functional unit, optionally with an integrated switch or sensor,
- optionally an indicator/actuator/signal generator,
- optionally a transmitter,
- optionally a receiver.

The functional unit may be flexible in its functionality and may for instance comprise one or more of the following:

- a timer, optionally with a programming interface,
- an indicator function for allowing the medical device to be found/located (for instance like a key finder), optionally in combination with an external transmitter or an external activation
- an RFID unit and/or a storage medium.

Examples of the indicator/actuator/signal generator may for instance function in one or more of the following ways:

- optically, for instance via an LED,
- acoustically (for instance speech generation or sound signal),
- by means of oscillation, for instance by vibration,
- via a data set, for instance comprising one or more of an expiration date, a production date, an indication of the type of medicament, an active ingredient of the medicament, a serial number.

In the following, an embodiment of the present invention will be described with reference to an insulin injection device, to which a module (as an embodiment of an apparatus according to the present invention) is attachable or attached. The present invention is however not limited to such application and may equally well be deployed with injection/infusion devices that eject other medicaments, or with other types of medical devices.

FIG. 1 is an exploded view of an injection device 1 and a module 2. Injection pen 1 may for instance represent Applicant's ClikSTAR® insulin injection pen.

Injection device 1 of FIG. 1 is a reusable injection pen that comprises a housing 10 and contains an insulin container 14, to which a needle 15 can be affixed. Insulin container 14 contains a cartridge (not detailed in FIG. 1) that actually contains the insulin and can be replaced with a new cartridge when empty, making injection device 1 reusable. The needle 15 is protected by an inner needle cap 16 and an outer needle cap 17, which in turn can be covered by a cap 18.

An insulin dose to be ejected from injection device 1 can be selected by turning the dosage knob (dosage selector) 12, and the selected dose is then displayed via dosage window 13, for instance in multiples of so-called International Units (IU), wherein one IU is the biological equivalent of about 45.5 µg pure crystalline insulin (1/22 mg). An example of a selected dose displayed in dosage window 13 may for instance be 30 IUs, as shown in FIG. 1.

Turning the dosage knob 12 may cause a mechanical click sound to provide acoustical feedback to a user. The numbers displayed in dosage window 13 are printed on a sleeve that is contained in housing 10 and mechanically interacts with a piston in insulin container 14 (and the cartridge contained therein). When needle 15 is stuck into a skin portion of a patient, and then actuation button (injection button) 11 is pushed inwards, for instance by a thumb of the user of injection device, the insulin dose displayed in display window 13 will be ejected from injection device 1. When the needle 15 of injection device 1 remains for a certain time in the skin portion after the injection button 11 is pushed, a high percentage (or even all) of the dose is actually injected into the patient's body.

Injection device 1 may be used for several injection processes. As stated above, an empty insulin cartridge (positioned in insulin container 14) can be replaced by a new one.

Before using injection device 1 for the first time (or after a change of the cartridge), it may be necessary to perform a so-called "prime shot" to remove air from the cartridge in insulin container 14 and needle 15, for instance by selecting two units of insulin and pressing actuation button 11 while holding injection device 1 with the needle 15 upwards.

In FIG. 1, further a module 2 is shown, which is attachable to actuation button 11 of injection device 1, for instance by clicking or pressing it onto actuation button 11, for instance to achieve a form closure or fit closure. Equally well, module 2 may be screwed on actuation button 11, or may be glued thereon.

This may for instance be performed by a user of injection device 1, and may lead to either a fixed or releasable connection between module 2 and injection device 1. As already described above, module 2 may equally well be attached (either fixedly or releasably) to injection device 1 during production of injection device 1. Module 2 comprises a detector unit with a detector that detects an actuation action performed to actuation button 11, and an electric unit for storing or providing information related to this detected actuation action.

Mounting module 2 on actuation button 11 has the advantage that module 2 can be affixed without requiring modification of the injection device 1, and that a robust detection of actuation actions can be achieved, since actuation actions can only be applied to actuation button 11 via module 2.

Figure 2:
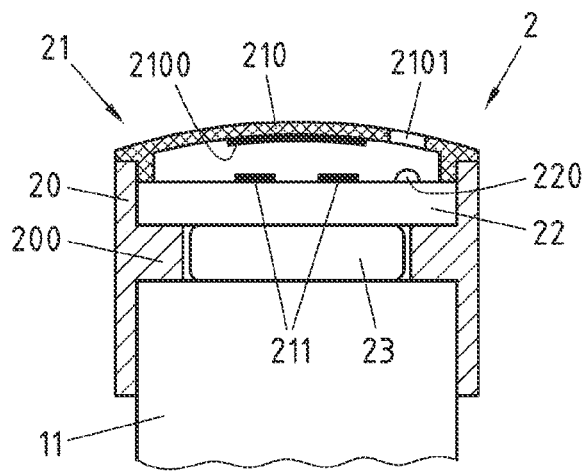
FIG. 2 shows a cross-sectional view of an embodiment of an apparatus according to the present invention.

FIG. 2 is a cross-sectional view through the centre of an embodiment of the module 2 of FIG. 1 when it is attached to actuation button 11 of injection device 1.

Module 2 comprises a housing 20, which is of cylindrical shape with a circular inner protrusion 200. Housing 20 may for instance be made of aluminium.

Above the circular protrusion 200 of housing 20, an electric circuit 22 is positioned. Electric circuit 22 may be attached to housing 20, for instance by gluing, but equally well, no specific attachment may be performed, for instance to allow electric circuit 22 to be removed from module 2, for instance to change electric circuit 22. Electric circuit 22 is for instance formed on a printed circuit board, which may have one or more layers of wiring. On top of electric circuit 22, a light emitting diode (LED) 220 is positioned, which is under control of the electric circuit 22.

Electric circuit 22 is connected to the poles of a battery 23 (e.g. a coin cell), which is positioned below electric circuit 22 and at least partially within circular protrusion 200, via contacts (for instance one or more contacts that contact battery 23 laterally (first pole) and one or more contacts that contact battery 23 at its top (second pole)) not shown in FIG. 2. Electric circuit 22 is thus powered by battery 23. Battery 23 may for instance be held in circular protrusion 200 (for instance a battery holder with included contacts, which may for instance be attached to or formed on the bottom of electric circuit 22) and may be removed, for instance for replacement, by pulling it downwards out of circular protrusion 200.

On top of electric circuit 22, contact areas 211 are formed, which are connected to electric circuit 22 as will be discussed with reference to FIG. 3 below. Module 2 further comprises a snap disk 210, which has an electrically conductive portion 2100 on its lower side and is arranged with respect to contact areas 211 in way that if a downward force is applied to snap disk 210, snap disk 210 deforms and electrically conductive portion 2100 of snap disk 210 comes into contact with contact areas 211, so that these contact areas 211 are electrically connected. Snap disk 210 and contact areas 211 thus form an electric switch 21, which functions as a detector for a force applied to snap disk 210. A reset force for this electric switch 21 is provided by snap disk 210 in a way that, if the downward force is no longer applied to snap disk 210, snap disk 210 returns into its previous position. Snap disk 210 is designed to be at least partially transparent, so that light emitted by LED 220 can be perceived through snap disk 210. To this end, snap disk 210 may for instance have circular or ring-shaped transparent areas. In FIG. 2, such a circular transparent area 2101 is indicated in snap disk 210.

Below the circular protrusion 200 of housing 20, module 2 forms a circular space for absorption of at least a part of actuation button 11 of injection device 1. This space may at least partially also be used by a lower portion of battery 23. The radius of this circular space is adapted to the outer radius of actuation button 11 in a way that module 2 can be attached to actuation button 11 and firmly rests on actuation button 11, while still being releasable from actuation button 11 without destroying module 2 and actuation button 11, for instance if injection device 1 is replaced by another injection device, but module 2 shall be reused.

Example measures for the module 2 of FIG. 2 are a total height of 10.67 mm, with the height of the housing above the circular protrusion being 3 mm, and the height of the housing below the circular protrusion being 5.4 mm. The total diameter of module 2 may for instance be 17 mm, and the inner diameter of circular protrusion 200 may for instance be 11 mm.

Functionally, electric switch 21, electric circuit 22, battery 23 and the upper part of the housing 20 with circular protrusion 200 form a detector unit. An actuation action (which in the present embodiment corresponds to an actuation force) can be exerted to actuation button 11 of injection device 1 only via this detector unit and is detected by switch 21 that functions as a detector. In case that battery 23 is not in contact with actuation button 11 (unlike the example shown in FIG. 2), the detector unit may be considered to only comprise electric switch 21, electric circuit 22 and the upper part of housing 20 with circular protrusion 200, since these components relay the actuation force to actuation button 11.

Switch 21 is configured to detect the actuation action based on a detection of a force applied to the detector unit as part of the actuation action. In particular, when desiring to cause ejection of a selected dose of the medicament contained in injection device 1, the actuation force is initially applied to snap disk 210, which is then pushed downward to come into contact with contact areas 211. The actuation force is then relayed to circular protrusion 200 via the electric circuit 22 and battery 23, and then relayed to its actual destination, the actuation button 11, via the circular protrusion 200.

It is readily clear for a person skilled in the art that a plurality of alternatives exists for the arrangement of components shown in FIG. 2. For instance, to avoid that the actuation force has to be applied to actuation button 11 inter alia via the electric circuit 22 (and, as shown in FIG. 2, battery 23), which may cause damages to these components, contact areas 211 may for instance not be formed on top of electric circuit 22, but on a separate carrier plate, to which also the snap disk 210 is connected. This carrier plate may then for instance only be in contact with the electric circuit 22 at an outer region thereof (i.e. near housing 20), so that an actuation force applied to this carrier plate may then be relayed only to the outer region of electric circuit 22 and thus may avoid damage of components in the inner region of electric circuit 22.

Equally well, of course other types of electric switches may be used. For instance, instead of snap disk 210, a rigid plate or cap (e.g. convex or concave) may be used attached on top of housing 20 and with a central opening through which an actuator of an electric switch (e.g. a key switch) protrudes, wherein the length of the way the actuator has to be moved down to close the electric switch is chosen so that the switch is closed when the top of the actuator and the top surface of the plate are aligned, and that in this position and also when applying further force on the plate, only the reset force of the switch (for instance cause by a reset spring) acts on components to which the switch is mounted. When applying an actuation force via this plate, then the actuator of the electric switch is pressed inwards and the electric switch is closed. Further applying the actuation force then leads to the actuation force being relayed to the actuation button 11 via the housing 20 and its protrusion 200, and not via the electric circuit 22 and the battery 23.

Equally well, of course other types of detectors may be deployed, such as for instance a touch sensor arranged on, in or below a plate (or cap) placed on top of housing 20, or a pressure sensor that is arranged within housing 20 and is responsive to changes in pressure caused with an upper part of housing 20 when a force is applied to a flexible membrane or other moving member attached to the top of housing 20 (assuming that housing 20 is otherwise tight, which may for instance be achieved by replacing protrusion 200 by a solid plate).

In the module 2 of FIG. 2, the electric circuit 22 is connected to switch 21, in particular to its contact areas 211, and provides information related to the actuation action detected when switch 21 is closed. In the embodiment of FIG. 2, electric circuit 22 implements a timer that is activated when switch 21 is closed and turns on LED 220 for a pre-defined time. Lighting of the LED 220 thus indicates to a user of injection device 1 that a pre-defined time period since a last actuation action has not yet passed, and thus may for instance prevent too early reuse of the injection device 1, for instance in case that the user forgot that he already used the injection device 1 shortly before.

Figure 3:
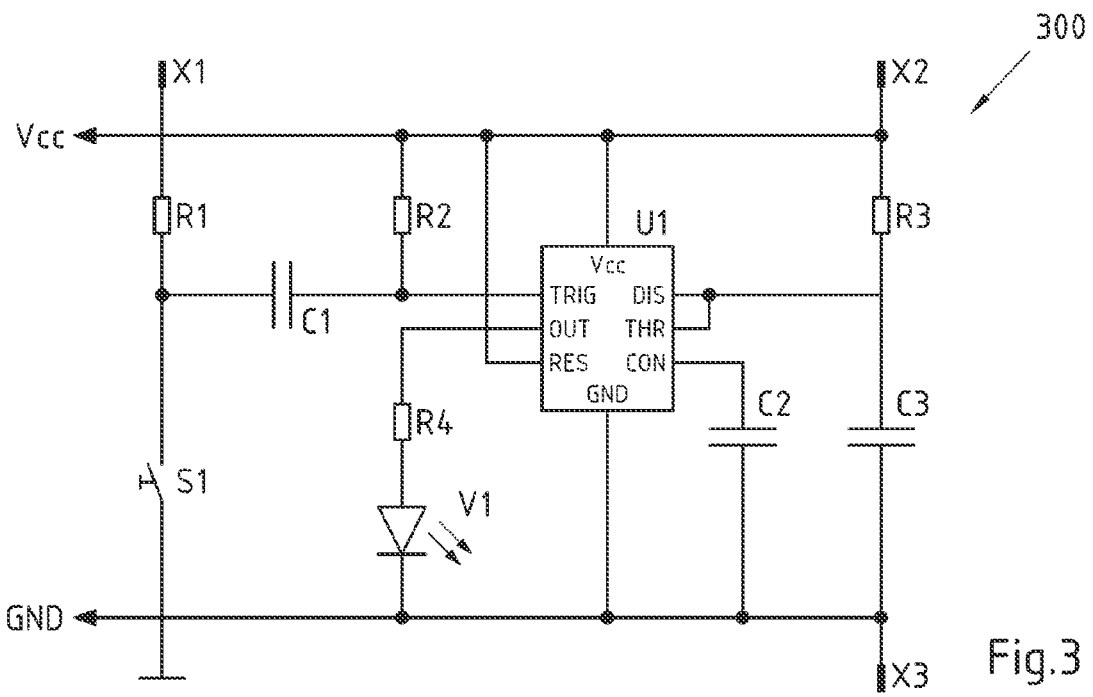
FIG. 3 shows an embodiment of a circuit diagram of an electric unit of an apparatus according to the present invention.

FIG. 3 shows an example of a circuit diagram 300 for the electric circuit 22 of module 2 of FIG. 2.

The electric circuit implements a monostable multivibrator with a timer element U1 (such as for instance Texas Instruments' TLC555, which is a low-power variant of an NE555 timer) at its core. X1 and X2 denote battery contacts connected to one pole of battery 23 (supply voltage potential Vcc). These two contacts may for instance contact battery 23 laterally. X3 is a battery contact connected to the other pole of battery 23 (ground potential GND), which may for instance be arranged at the top of battery 23. Battery 23 may for instance be a coin cell battery, such as for instance of type CR1025.

In circuit diagram 300, S1 represents electric switch 21 of FIG. 2, and V1 denotes LED 220 of FIG. 2. Furthermore, R1, R2, R3 and R4 are resistors, and C1, C2 and C3 are capacitors.

The electric circuit of FIG. 3 functions as follows: If switch S1 is closed, LED V1 is turned on and emits light. After a pre-defined time, which is governed by the values of R3 and C3 (T=R*C), LED V1 is turned off again.

For instance, the pre-defined time may be set to 15 minutes. LED V1 then is active for 15 minutes after the last use of the injection device 1 and in this way reminds a user that injection device 1 has already been used.

As already stated above, indication that a pre-defined time duration since the last actuation action has not yet passed is only one example of additional functionality that can be added to an injection device according to embodiments of the present invention. Equally well, module 2 may be modified to convey other information. For instance, the time instant of the last detected actuation action (or a history of the last detected actuation actions) may be indicated to a user, for instance optically (via a display integrated into module 2) or acoustically (for instance via speech generation or via sounds). This indication may for instance be performed in response to a request of the user, which may for instance be made by the user by pressing a button. Equally well, information on detected actuation actions (e.g. the last detected actuation action, or a history of the last detected actuation actions) may be stored in a memory of module 2, and/or may be provided to electronic devices via wired or wireless connections. The module 2 may also be equipped with a key finder functionality.

Electric circuit 23 of module 2 may also comprise a processor (such as for instance a microprocessor) that controls functions of module 2. This processor may for instance store and/or provide information related to an actuation action detected by a detector, such as for instance an electric switch (e.g. switch 21) or any other type of detector.

Figure 4:
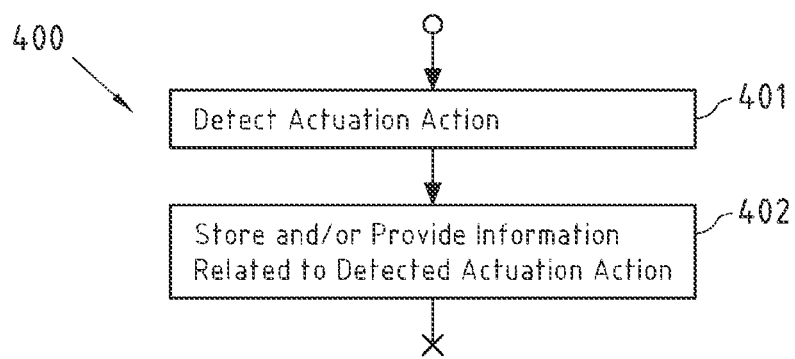
FIG. 4 shows a flowchart of an embodiment of a method according to the present invention.

FIG. 4 is a flowchart 400 of an embodiment of a method according to the present invention. This method may for instance be at least partially controlled and/or performed by a processor of module 2. A computer program with instructions operable to cause the processor to perform this may be stored on a computer-readable medium, which may for instance be a tangible storage medium. In a step 401, an actuation action is detected, and in a step 402, information related to the detected actuation action is stored and/or provided.

Module 2 of FIG. 2 may furthermore be equipped with a further component that is capable of measuring a dose that is dialed with dosage knob 12 (see FIG. 1). This component may for instance be formed on or attached to a lower portion of module 2 and may comprise a rotatable member that is attached to dosage knob 12 so that rotation thereof with respect to module 2 can be sensed. Information on this sensed rotation may then be transformed by the electric circuit 22 (or a processor of module 2) into information on a selected dose and may be stored and/or provided like the information on a detected actuation action. Alternatively, an acoustic sensor may be used in module 2 to determine a selected dose based on click sounds produced by injection device 1 when a dose is dialed.

The rotation may be measured relative to another part of the knob 12 or relative to a part of the injection device 1, for example relative to the housing 10, or relative to the dose dial sleeve that can be seen through the dosage window 13. By measuring the relative movement, it can be distinguished whether the dialed dose is measured or whether the injected dose is measured. In an example embodiment, dosage knob 12 may be rotated during dose dialing relative to housing 10, however it may not rotate relative to the housing 10 during dose injection. Thus, a dialed dose can be measured.

In an example embodiment, dosage knob 12 may be rotated during dose dialing relative to housing 10, but no rotational movement is made relative to the dose dial sleeve. During dose injection, the dose dial sleeve rotates. Thus, a relative rotational movement between the dose dial sleeve and the dosage knob may be detected during dose injection. As the module 2 is fixed to the dosage know 12, it may detect the relative movement.

The invention has been described above by means of embodiments, which shall be understood to be non-limiting examples only. In particular, it should be noted that there are alternative ways and variations which are obvious to a skilled person in the art and can be implemented without deviating from the scope and spirit of the appended claims.

The invention claimed is:

1. A medical device comprising:
a module comprising:
   a switch configured to detect an actuation action of a medical device, the actuation action causing the medical device to eject at least a portion of a medicament in the medical device, and
   an electric unit connected to the switch and configured to store and/or provide information related to the detected actuation action;
a housing;
a dosage knob configured for rotation relative to the housing during dose dialing and configured not to rotate relative to the housing during dose injection; and
a dose dial sleeve,
wherein the medical device is an injection device,
wherein the module is attached to the dosage knob,
wherein during the dose dialing, the dosage knob and the dose dial sleeve are stationary relative to one another, and during the dose injection, the dose dial sleeve rotates relative to the dosage knob, and
wherein a relative rotational movement between the dose dial sleeve and the dosage knob is detected by the module during the dose injection.

2. The medical device according to claim 1, wherein the dosage knob is configured to be rotated around a longitudinal axis of the medical device to select a dose of the medicament.

3. The medical device according to claim 2, wherein the module comprises a rotatable member that is configured for attachment to the dosage knob.

4. The medical device according to claim 1, comprising a medicament container configured to contain a cartridge of the medicament.

5. The medical device according to claim 1, wherein the dosage knob is configured to be turned to select a dose of the medicament to be ejected by the medical device.

6. A medical device comprising
a housing;
a container configured to contain a cartridge of a medicament;
a dosage selector configured to be rotated around a longitudinal axis of the medical device to select a dose of the medicament;
a dose dial sleeve configured to rotate during dose injection; and
a module comprising a detector to detect a rotational movement of the dose dial sleeve relative to the dosage selector during the dose injection, the module comprising a switch configured to detect an actuation action of a medical device, the actuation action causing the medical device to eject at least a portion of the medicament in the cartridge.

7. The medical device according to claim 6, comprising an optical sensor.

* * * * *